United States Patent [19]

Aderka et al.

[11] Patent Number: 5,462,731

[45] Date of Patent: Oct. 31, 1995

[54] USE OF IL-6 FOR THE TREATMENT OF CHRONIC LYMPHOCYTE LEUKEMIA (CLL) AND B-CELL LYMPHOMAS

[75] Inventors: Dan Aderka, Holon; Yasmin Maor, Raanana; David Wallach; Michel Revel, both of Rehovot, all of Israel

[73] Assignee: Yeda Research and Development Company Ltd., Rehovot, Israel

[21] Appl. No.: 963,313

[22] Filed: Oct. 20, 1992

[30] Foreign Application Priority Data

Oct. 20, 1991 [IL] Israel ............................................ 99803

[51] Int. Cl.$^6$ ........................... A61K 45/05; A61K 37/00
[52] U.S. Cl. .......................... 424/85.2; 424/85.1; 514/12; 514/21; 530/351
[58] Field of Search .................................. 424/85.2, 85.1; 514/12, 21; 530/351

[56] References Cited

U.S. PATENT DOCUMENTS

| | | | |
|---|---|---|---|
| 5,087,448 | 2/1992 | Burstein | 424/85.2 |
| 5,126,325 | 6/1992 | Kishimoto et al. | 514/12 |

FOREIGN PATENT DOCUMENTS

| | | | |
|---|---|---|---|
| 0356180 | 2/1990 | European Pat. Off. | A61K 37/02 |
| 0413908 | 6/1990 | European Pat. Off. | C12P 21/02 |
| 9006370 | 6/1990 | WIPO | C12P 21/00 |

OTHER PUBLICATIONS

Chen, L. et al., "Growth inhibition of human breast carcinoma and leukemia/lymphoma cell lines by recombinant interferon-$\beta_2$", Proc. Natl. Acad. Sci USA 85:8037–8041 (Nov. 1988).

Freeman, G. et al., "Interleukin 6 Gene Expression in Normal and Neoplastic B Cells", J. Clin. Invest 83 No. 5:1512–1518 (May 1989).

Chronic Lymphocytic Leukemica: New Insights into Biology and Therapy; Annals of Internal Medicane, 1990; vol. 113, No. 7, pp. 525–539.

British Journal of Haematology, 1984, 57, 105–111; Kay et al: Defective Expression of T Cell Antigens in Chronic Lymphocytic Leukemia: Relationship to T Cell Dysfunction.

Blood, vol. 57, No. 3 (Mar.), 1981; Neil Kay: Abnormal T–Cell Sybpopulation Function in CLL: Excessive Suppressor (Tr) and Deficient Helper (Tu) Activity with Respect to B–Cell Proliferation.

The Journal of Immunology, vol. 129, No. 5, Nov. 1992; pp. 2305–2312; "Abnoraml T Lymphocyte Subpopulations in Patients with B Cell Chronic Lymphocytic Leukemia: An Analysis by monoclonal Antibodies". Chris D. Platsoucas et al.

Blood, vol. 54, No. 2 (Aug.) 1979; Kay et al: T–Cell Subpopulations in Chronic Lymphocytic Leukemia: Abnormalities of Distribution and in in Vitro Receptor Maturation.

Americal Journal of Hematology 30:61–67(1989); Alan R. Liss, Inc.: Malignant Chronic Lymphocytic Leukemia B Cells Eleaborate Soluble Factors that Down–Regulate T–Cell and NK Function. Burton et al.

The Journal of Immunology, vol. 131, No. 2, Aug. 1983; Falkoff et al: The Effects of Interleukin 1 on Human B Cell Activation and Proliferation.

The New England Journal of Medicine, Juliusson et al, Sep. 13, 1990; Prognostic Subgroupes in B–Cell Chronic Lymphocytic Leukemia Defined by Specific Chromosomal Abnormalities.

J. Exp. Med., The Rockefeller Univ. Press, vol. 165, Mar. 1987; Brief Definitive Report; Identification of The Human 26–kD Protein, Interferon $B_2$ (IFN–$B_2$), As A B Cell Hybridomas/Plasmacytoma Growth Factor Induced by Interleukin 1 and Tumor Necrosis Factor.

J. Exp. Med., The Rockefeller Univ. Press, vol. 167, Feb. 1988, 332–344; Muraguchi et al: The Essential Role B Cell Stimulatory Factor 2 (BSF–2/IL–6) For the Terminal Differentiation of B Cells.

Nature, vil. 332, Mar. 3, 1988; pp. 83–84; Autocrine Generation and Requirement of BSF–2/IL–6 For Human Multiple Myelomas. Kawano et al.

The Lancet, Apr. 30, 1988; Cordingley et al.: Tumor Necrosis Factor as an Autocrine Tumour Growth Factor for Chronic B–Cell Malignancies.

Blood, vol. 73, No. 5 (Apr.), 1989; pp. 1242–1246; Digel et al: Tumor Necrosis Factor Induces Proliferation of Neoplastic B Cells from Chronic Lymphocytic Leukemia.

Blood, vol. 73, No. 5 (Apr.), 1989, pp. 1279–1284; Biondi et al.; Constitutive Expression of the Interleukin–6 Gene in Chronic Lymphocytic Leukemia.

Journal of Hematologie, (1988), pp. 317–318; ACM Bianchi; Dept. of Haematology: Effects of Tumor Necrosis Factor and a Interferon on Chronic B Cell Malignancies.

J. Exp. Med., The Rockfeller Univ. Press, vol. 172, Dec. 1990; pp. 1729–1734; Effects of Interferon $\alpha$ on Autocrine Growth Factor Loops in B Lymphoroliferative Disorders; Heslop et al.

The Journal of Immunology, vol. 140, No. 12, Jun. 15, 1988; pp. 4329–4336; Tosato et al.: Stimulation of EBV–Activated Human B Cells by Monocytes and Monocyte Products.

Cell, vol. 58, 573–581, Aug. 11, 1989; Taga et al.: Interleukin–6 Triggers the Association of its Receptor with a Possible Signal Transducer, gp130.

Journal of Immunological Methods, 33(1980) 323–336; Madselen et al.: Isolation of Human T and B Lymphocytes by E–Rosette Gradient Centrifugation. Characterization of the Isolated Subpopulations.

(List continued on next page.)

Primary Examiner—Michael G. Wityshyn
Assistant Examiner—Abdela Mohamed
Attorney, Agent, or Firm—Browdy and Neimark

[57] ABSTRACT

The use of interleukin-6 and/or salts, functional derivatives, muteins or active fractions thereof, in the treatment of chronic lymphocytic leukemia and B-cell lymphomas, as well as such use together with the soluble interleukin-6 receptor, to pharmaceutical compositions and to a method of treating chronic lymphocytic leukemia or B-cell lymphomas.

7 Claims, 13 Drawing Sheets

OTHER PUBLICATIONS

Cellular Immunology 58, 426–435 (1981); Fischer et al.: Tumor Cell Killing by Freshly Isolated Peripheral Blood Monocytes.

The Journal of Immunology, vol. 143, 3517–3523, No. 11, Dec. 1, 1989; IL–6 Inhibits Lipopolysaccharide–Induced Tumor Necrosis Factor Production in Cultured Human Monocytes, U937 Cells, and in Mice. by Aderka et al.

Blood, vol. 75, No. (Jan. 1), 1990; pp. 40–47; Schindler et al.: Correlation and Interactions in the Production of Interleukin–6 (IL–6), Il–1; and Tumor Necrosis Factor (TNF) in Human Blood Mononuclear Cells: IL–6 Suppresses IL–1 and TNF.

Cancer Research 51, pp. 5602–5607, Oct. 1991; Aderka et al.: Increased Serum Levels of Soluble Receptors for Tumor Necrosis in Cancer Patients.

Lahat et al, *Clin. Exp. Immunol.*, *vol. 85, No. 2, pp. 302–306, Aug. 1991*.

Schindler et al, *Blood*, vol. 75, No. 1, pp. 40–47, Jan. 1, 1990.

Aderha et al, *Blood*, vol. 81, No. 8, pp. 2076–2084, Apr. 15, 1993.

Hsu et al, *American Journal of Pathology*, vol. 141, No. 4, pp. 915–923, Oct. 1992.

Aguilar–Santelises, *Clin. Exp. Immunol*, vol. 84, No. 3, pp. 422–428, Jun. 1991.

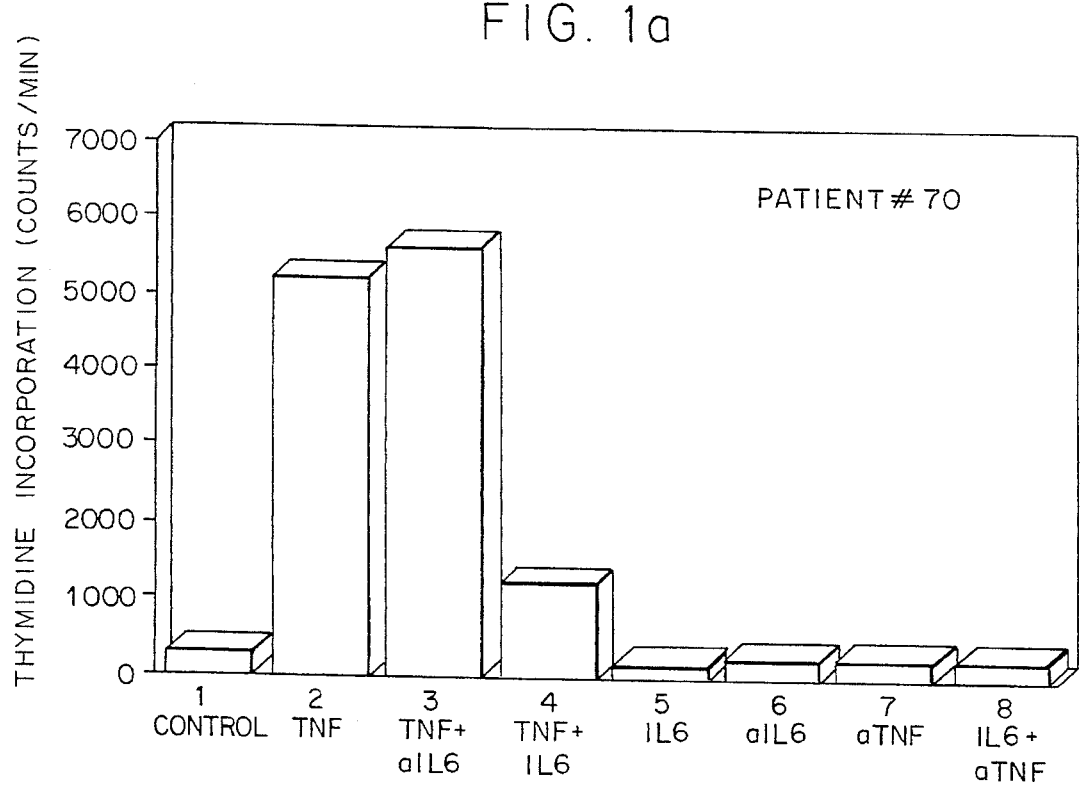
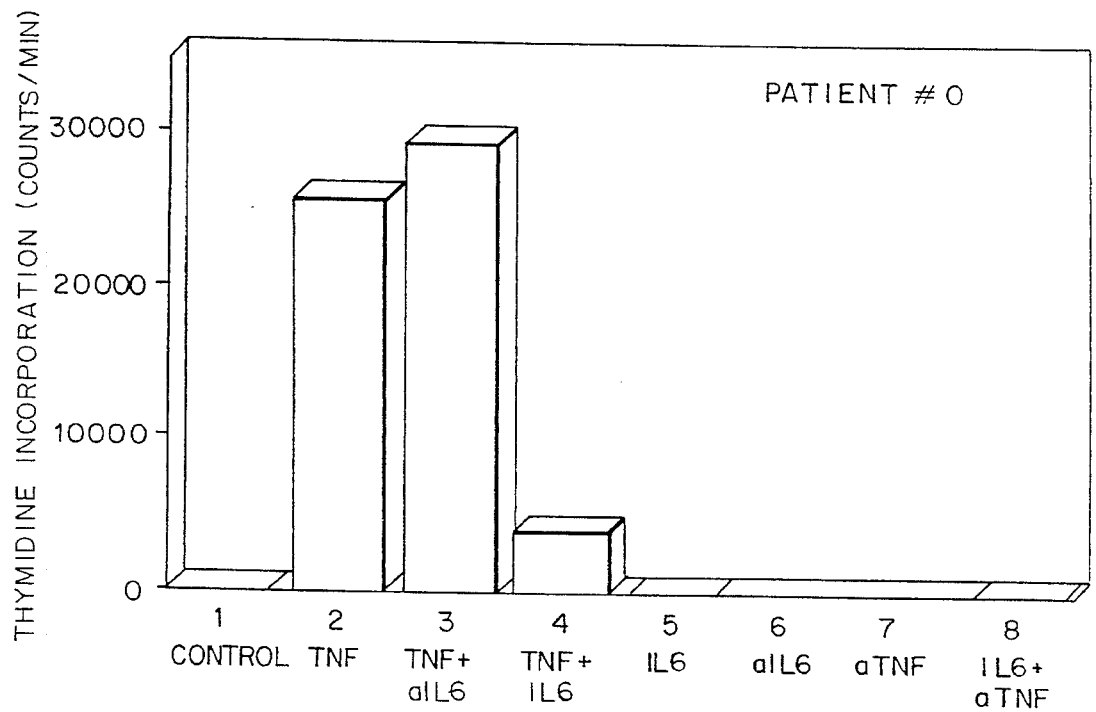

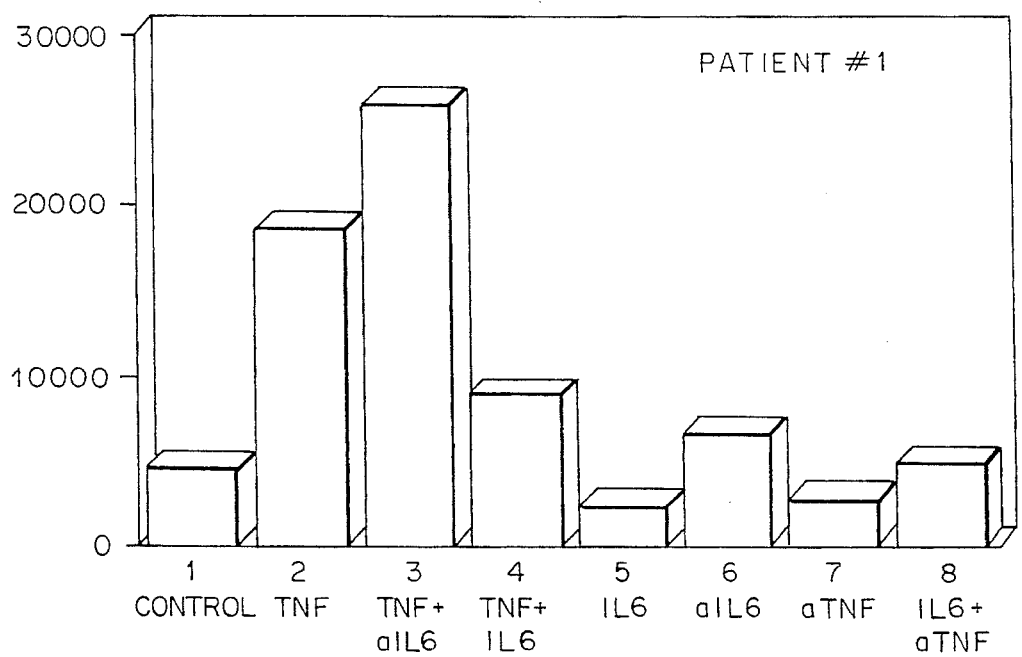
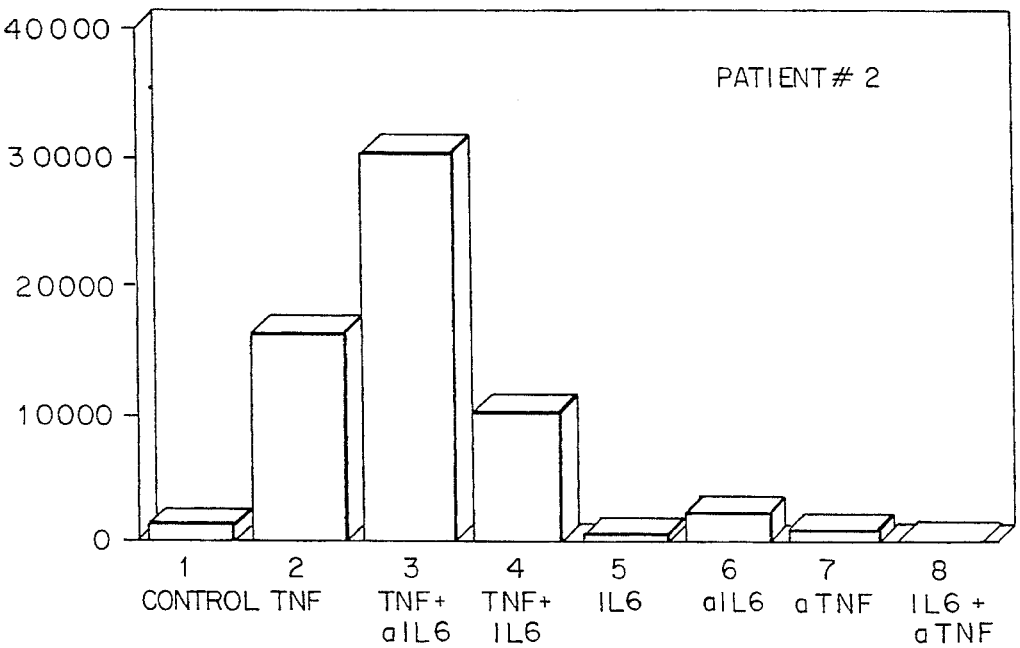

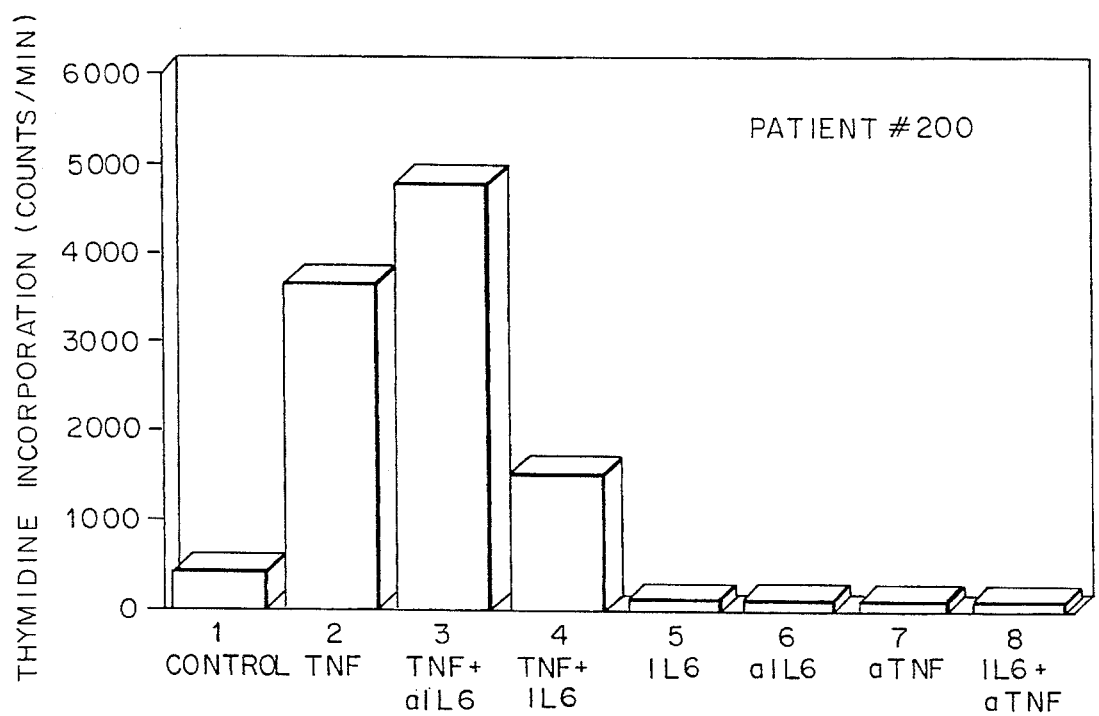

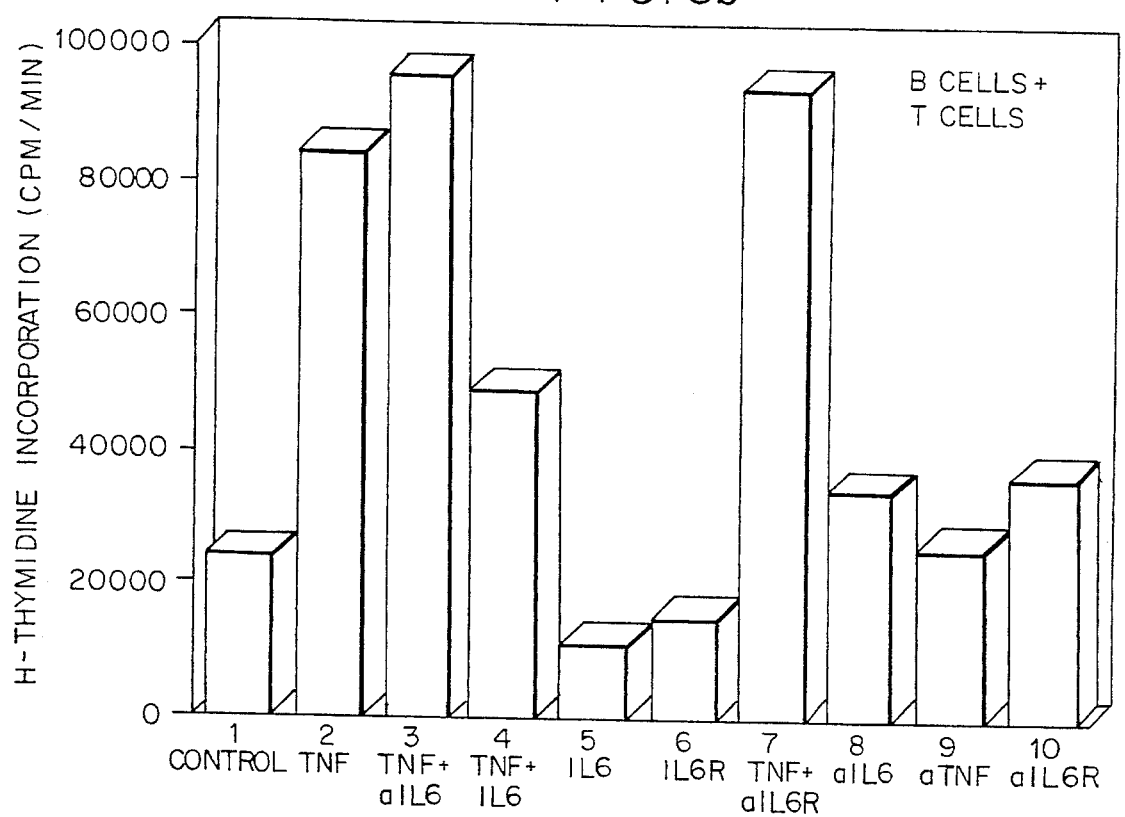
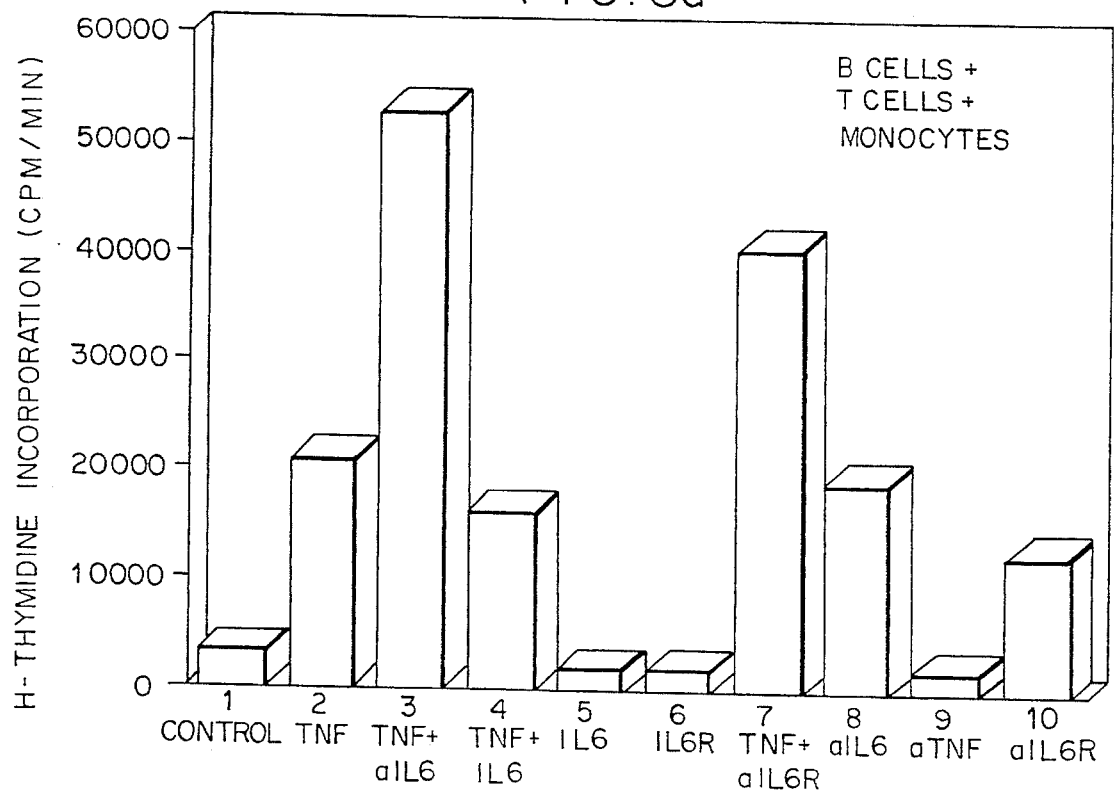

USE OF IL-6 FOR THE TREATMENT OF CHRONIC LYMPHOCYTE LEUKEMIA (CLL) AND B-CELL LYMPHOMAS

FIELD OF THE INVENTION

The present invention relates to the field of biotechnology and more specifically to the use of interleukin-6 and/or salts, functional derivatives, muteins or active fractions thereof, optionally with soluble interleukin-6 receptor peptides, in the treatment of chronic lymphocytic leukemia and B-cell lymphomas.

BACKGROUND OF THE INVENTION

B-cell neoplasms are a heterogeneous group of diseases characterized by different maturation states of the B-cell, which are related to the aggressiveness of the disorder. Accordingly, the lymphomas are classified into three groups: low grade, intermediate grade and high grade lymphomas. The "low grade" nodular lymphocytic, well-differentiated lymphoma is occasionally confused with chronic lymphocytic leukemia because of the identical histologic picture.

Chronic lymphocytic leukemia (CLL) is characterized by proliferation and accumulation of B-lymphocytes that appear morphologically mature but are biologically immature. CLL typically occurs in persons over 50 years of age. This disorder accounts for 30% of leukemias in Western countries, with 10,000 new cases being diagnosed annually in the United States alone[1].

The disorder is characterized by proliferation of biologically immature lymphocytes, unable to produce immunoglobulins, which upon organ infiltration cause lymph-node enlargement and hepato-splenomegaly. In the advanced stages of the disease, bone marrow occupation by the abnormal lymphocytes results in bone marrow failure, resulting in anemia and thrombocytopenia.

The B-cells in CLL have receptors for mouse erythrocytes, a marker of immature B-cells. An increased number of T-cells has been reported in this disorder with an increase in the number of T-suppressor cells[2-5]. Some data support the possibility that B-CLL cells secrete an inhibitory factor that suppresses T-cell function[6]. In addition, in 50% of CLL patients, chromosome analysis provides prognostic information about overall survival, in addition to that supplied by clinical data in patients with B-cell CLL[7].

Several cytokines have been reported to stimulate the growth of B-cells in general, such as interleukin-1[8] and interleukin-6[9-11] (hereinafter IL-6), while tumor necrosis factor (TNF) have been shown to serve as an autocrine tumor growth factor for the pathological B-cells in CLL[12, 13].

IL-6 has been found to serve also as a growth stimulatory factor for certain B-cell neoplasms such as plasmacytoma, myeloma cells and derived hybridomas[9-11] or for Epstein-Barr virus (EBV)-transformed B lymphocytes[17]. In B-cell CLL, constitutive expression of the IL-6 gene was found, but the biological significance of IL-6 expression in B-CLL was not fully elucidated[14].

As mentioned above, TNF has been shown to serve as an autocrine tumor growth factor for B-cell CLL[12, 13], prolonging the survival of B-cell CLL cells and inducing them to proliferate[15].

mRNA for IL-6 is induced by TNF in B-CLL cells; this cytokine could then be the agent responsible for the proliferative events of the leukemic cells. If B-cell CLL is dependent on autocrine growth factors for survival, interruption of the autocrine loop would be of therapeutic value[15]. Such interruption of the autocrine growth-stimulating loops was obtained with interferon-$\alpha$[16], yet administration of this cytokine to CLL-patients was not beneficial.

IL-6 does not promote the growth of normal B-lymphocytes. Since the growth effect of IL-6 is seen in EBV transformed cells or in B-cell tumors, it was anticipated that the growth of leukemic B-cells from CLL patients will also be stimulated by this cytokine.

SUMMARY OF THE INVENTION

Contrary to expectations in the relevant art, the present invention provides the unexpected result that the TNF induced proliferation of the leukemic lymphocytes from CLL patients (as measured by $^3$H-thymidine incorporation) is inhibited by the administration of IL-6, in vivo, in vitro, and in situ.

The present invention thus relates to the discovery that IL-6 inhibits TNF-$\beta$ and TNF-$\beta$ (hereinafter both will be designated "TNF") induced proliferation of leukemic lymphocytes from CLL patients.

The present invention thus relates to the use of IL-6 and/or salts, functional derivatives, muteins or active fractions thereof, in the manufacture of a pharmaceutical composition for the treatment of CLL or B-cell lymphomas.

In another aspect, the invention relates to the use of IL-6 and/or salts, functional derivatives, muteins or active fractions thereof, together with the soluble IL-6 receptor, in the manufacture of a pharmaceutical composition for the treatment of CLL or B-cell lymphomas.

In yet another aspect, the invention relates to pharmaceutical compositions for the treatment of CLL or B-cell lymphomas, comprising IL-6 and/or salts, functional derivatives, muteins or active fractions thereof, as active ingredients, optionally together with pharmaceutically acceptable carriers and/or excipients and/or adjuvants.

The pharmaceutical compositions may also comprise the soluble IL-6 receptor as a further active ingredient.

The invention also relates to a method for treating CLL or B-cell lymphomas, comprising administration of a pharmaceutically effective amount of IL-6, and/or salts, functional derivatives, muteins or active fractions thereof to a patient, optionally together with the soluble IL-6 receptor and with pharmaceutically acceptable carriers and/or excipients and/or adjuvants.

BRIEF DESCRIPTION OF THE DRAWINGS

FIGS. 1a–1d show the $^3$H-thymidine incorporation by CLL lymphocytes of 4 different patients in response to TNF, TNF and IL-6, TNF and anti-IL-6 antibodies, and the respective controls.

FIGS. 3a–c show that the effects of IL-6 from different sources exert similar influences on B-cell CLL cells.

FIGS. 8a–8d show the effects of TNF, IL-6, anti-IL-6 Ab, IL-6-R and their different combinations on 4 different cell populations: B-cells, B-cells+T-cells, B-cells+monocytes, and a combination of all three.

DETAILED DESCRIPTION OF THE INVENTION

Figure 2:
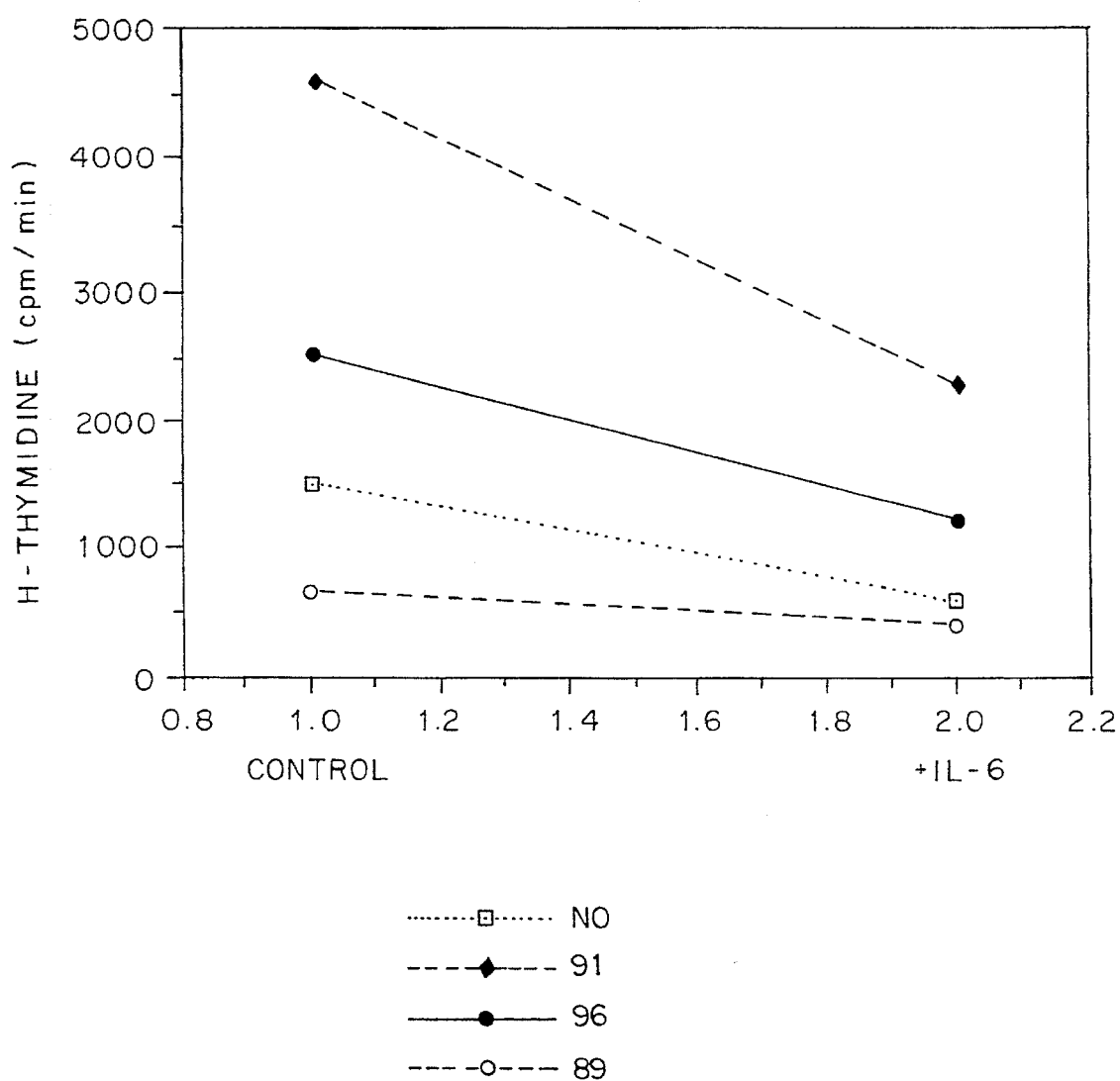
FIG. 2 shows reduction in $^3$H-thymidine incorporation in B-CLL cells treated with IL-6, compared to control cells (without exogenous TNF).

It was found in accordance with the present invention that the TNF-induced proliferation of leukemic lymphocytes from CLL patients (as determined by $^3$H-thymidine incorporation) is inhibited by IL-6. This IL-6 inhibition of TNF effects is even more pronounced in the presence of its soluble receptor (sIL-6 R), known to assist IL-6 in its biological activity[18]. See also European patent publication no. 413,908.

The inhibition of leukemic lymphocytes by IL-6 was demonstrated in a sub-group of CLL patients whose lymphocytes proliferate in the presence of TNF. The IL-6 induced inhibition of B-CLL lymphocytes is observed with autologous TNF as well as with its exogenous addition to cultures.

The invention shows that the autologous IL-6, optionally with sIL-6 R, production by the cells is important to partially or substantially inhibit or otherwise overcome the proliferative signals of TNF.

The IL-6, optionally with sIL-6 R, inhibition of the TNF growth stimulatory effects is further supported by two additional observations: (a) Neutralization of IL-6 by anti-IL-6 Ab, resulted in augmentation of the B-cell CLL lymphocyte proliferation in response to TNF; and (b) prevention of IL-6 action by neutralization of its cell-associated receptor with anti-IL-6 Receptor Ab, resulted in a sharp increase in the proliferation of the leukemic lymphocytes as determined by $^3$H-thymidine incorporation.

The inhibition by IL-6, optionally with sIL-6 R, of TNF-induced growth and proliferation B-cell CLL lymphocytes can be exploited clinically to arrest and possibly to induce remission in CLL.

IL-6, optionally with sIL-6 R, can also increase the number of thrombocytes in this disease and augment immunoglobulin production, which are impaired in this disorder.

In the context of the present invention the terms "interleukin-6" or "IL-6", and/or "soluble interleukin-6 receptor" or "sIL-6 R" are intended to encompass any isolated or purified IL-6 and/or sIL-6 R that is chemically synthesized or derived from recombinant host cells expressing IL-6 and/or sIL-6 R or obtained from tissue or cells which express IL-6 and/or sIL-6 R, which includes any polypeptides or proteins having IL-6 and/or sIL-6 R biological activity, including IL-6 and/or sIL-6 R salts, functional derivatives, active fractions or muteins. Methods for producing IL-6 and/or sIL-6 R are well known in the art. See, e.g., EPO Publication No. 0220574 to Revel et al.; U.S. Pat. Nos. 5,126,325 (Kishimoto et al); 5,087,448 (Burstein et al); 5,087,448 (assigned to the University of Oklahoma); PCT publication no. WO 88/00206 to Genetics Institute; PCT publication No. WO 90/06370 to Fowlkes et al.; EPO Publication No. 0 331 180 to Chui et al; and EPO publication No. 0413908 to Novick et al.

As used herein the term "salts" refers to both salts of carboxyl groups and to acid addition salts of amino groups of the protein molecule. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the pharmacological activity of the protein as described herein and do not confer toxic properties on compositions containing it. "Functional derivatives" also include derivatives which may have conservative amino acid substitutions, as well as additions and deletions, as long as they remain pharmaceutically acceptable, i.e., they do not destroy the pharmacological activity of the protein as described herein and do not confer toxic properties on compositions containing it.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

An amino acid sequence, or nucleic acid sequence encoding therefor, of an IL-6 or sIL-6 R salt, functional derivative, active fraction or mutein, to be used in accordance with the present invention, is a functional derivative of another amino acid or nucleic acid sequence, respectively, if the sequence of amino acids or nucleic acid in both molecules provides or includes polypeptides having IL-6 or sIL-6 R biological activity that is substantially similar, qualitatively or quantitatively, to the corresponding IL-6 or sIL-6 R polypeptide, protein or fragment, comprising at least one functional domain of a known IL-6 or sIL-6 R.

Additionally or alternatively, such functional derivatives of IL-6 or sIL-6 R sequences include conservative amino acid or nucleotide substitutions, or degenerate nucleotide codon substitutions, wherein individual amino acid or nucleotide substitutions are well known in the art, based on the teaching and guidance presented herein.

Alternatively or additionally, functional derivatives of IL-6 or sIL-6 R polypeptides or proteins having amino acid sequences are at least 80% homology or identity to an amino acid sequence of IL-6 and/or sIL-6 R having biological activity or contributing to conformation of the IL-6 and/or sIL-6 R, such as 80, 81, 82, 83, 84, 85, 86, 87, 88, 89, 90, 91, 92, 93, 94, 95, 96, 97, 98, 99 or 100% homology or identity.

Accordingly, functional derivatives of IL-6 or sIL-6 R polypeptides or proteins to be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, N.Y., 1978, and Creighton, T. E., *Proteins: Structure and Molecular Properties*, W. H. Freeman & Co., San Francisco, 1983, which are hereby incorporated by reference. For a presentation of nucleotide sequence substitutions, such as codon preferences, see Ausubel et al, supra, at §§A.1.1-A.1.24, and Sambrook et al, supra, at Appendices C and D.

Conservative amino acid substitutions of IL-6 or sIL-6 R polypeptides or proteins may include synonymous amino acids within a group which have sufficiently similar physicochemical properties that substitution between members of the group will preserve the biological function of the molecule, Grantham, *Science*, vol. 185, pgs. 862–864 (1974). It is clear that insertions and deletions of amino acids may also be made in the above-defined sequence without altering biological function, particularly if the insertions or deletions only involve a few amino acids, e.g., under ten, and do not remove or displace amino acids which are critical to a functional conformation, e.g., cysteine residues, Anfinsen, "Principles That Govern The Folding of Protein Chains", *Science*, Vol. 181, pgs. 223–230 (1973). Proteins and muteins produced by such deletions and/or insertions come within the purview of the present invention. Whenever amino acid residues of the protein of Formula I are referred to herein by number, such number or numbers are in reference to the N-terminus of the protein.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |

TABLE II-continued

More Preferred Groups of Synonymous Amino Acids

| Amino Acid | Synonymous Group |
|---|---|
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining functional derivatives of IL-6 or sIL-6 R polypeptides or proteins for use in the present invention include any known method steps, such as presented in U.S. Pat. Nos. RE 33,653, 4,959,314, 4,588, 585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

As "active fractions" of the IL-6 or sIL-6 R, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has the same biological activity as IL-6 and/or sIL-6 R and remains pharmaceutically acceptable.

"Muteins" are those proteins in which one or more amino acids of the IL-6 and/or sIL-6 R amino acid sequence have been replaced with another amino acid and/or deleted, provided that the resulting mutein exhibits the same biological activity as IL-6 and/or sIL-6 R and is pharmaceutically acceptable.

Such muteins, active fractions, functional derivatives or salts of IL-6 or sIL-6 R are intended to be encompassed by the terms "IL-6" or "sIL-6 R" as used herein.

The term "substantially corresponding to" is intended to comprehend proteins with minor changes to the sequence of the natural protein which do not affect the basic characteristics of the natural protein insofar as the pharmacological activity of the protein is concerned. The type of changes which are generally considered to fall within the "substantially corresponding to" language are those which would results from conventional mutagenesis techniques of the DNA encoding these proteins, resulting in a few minor modifications, and screening for the desired activity.

Pharmaceutical compositions for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods. See, e.g., Berkow et al, eds., *The Merck Manual*, 16th edition, Merck and Co., Rahway, N.J., 1992; Goodman et al., eds., *Goodman and Gilman's The Pharmacological Basis of Therapeutics*, 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Katzung, ed. *Basic and Clinical Pharmacology*, Fifth Edition, Appleton and Lange, Norwalk, Conn. (1992), which references and references cited therein, are entirely incorporated herein by reference.

Pharmaceutical compositions comprising IL-6, optionally with sIL-6 R polypeptides, may include all compositions wherein the IL-6, optionally with sIL-6 R, is contained in an amount effective to achieve its intended purpose. In addition to at least one IL-6, optionally with sIL-6 R, a pharmaceutical composition may contain suitable pharmaceutically acceptable carriers, such as excipients, carriers and/or auxiliaries which facilitate processing of the active compounds into compositions which can be used pharmaceutically.

Pharmaceutical compositions comprising at least one IL-6, optionally with at least one sIL-6 R, may also include suitable solutions for administration intravenously, subcutaneously, dermally, orally, mucosally or rectally and may be administered by injection or orally, and contain from about 0.01 to 99 percent, preferably from about 20 to 75 percent of active component together with the excipient. Pharmaceutical compositions for oral administration include tablets and capsules. Compositions which can be administered rectally include suppositories. See, e.g., Berker, supra, Goodman, supra, Avery, supra and Ebadi, supra, which are entirely incorporated herein by reference, included all references cited therein.

Pharmaceutical compositions according to the invention are administered via the accepted ways of administration. Preferred ways of administration are intravenous, intramuscular or subcutaneous. The pharmaceutical compositions may also be administered continuously, i.e., by way of fusion. The formulation and dose will depend on the condition to be treated, the route of administration and the condition and the body weight of the patient to be treated. The exact dose will be determined by the attending physician.

The pharmaceutical compositions according to the invention are prepared in the usual manner, for example by mixing the active ingredient with pharmaceutically and physiologically acceptable carriers and/or stabilizers and/or excipients, as the case may be, and are prepared in dosage form, e.g., by lyophilization in dosage vials. As used herein, the term "pharmaceutically acceptable" refers to a carrier medium which does not interfere with the effectiveness of the biological activity of the active ingredients and which is not toxic to the hosts to which it is administered.

The following examples illustrate the invention without limiting it thereto:

EXAMPLE 1

IL-6 Inhibits TNF Induced Proliferation of Leukemic B-CLL Cells

Mononuclear leukocytes of B-chronic lymphocytic leukemia (B-CLL) patients were isolated from the peripheral blood by centrifugation on a Ficoll-Hypaque cushion (Pharmacia, Uppsala, Sweden). To enrich the leukocyte fraction of leukemic cells, the mononuclear leukocytes were depleted of T-cells by rosetting with sheep erythrocytes[19], and then further depleted of the mononuclear phagocytes by adherence to plastic[20]. The leukocytes were cultured in RPMI 1640 medium, supplemented with 10% fetal calf serum.

B-CLL cells were cultured in 96-well microtiter plates at densities of $2.5 \times 10^5$ cells/0.2 ml/well and $5 \times 10^3$ cells/0.2 ml/well respectively. The rate of cell growth following the indicated culture time was assessed by measuring the incorporation of $^3$H-thymidine into the DNA of the cells. Labelled thymidine (25 Ci/mmole, Amersham, UK) was applied to the cultures (1 µCi/well) for the last 8 hrs. of incubation and the amount of radioactivity incorporated into DNA was then determined after harvesting the cells with the aid of a PHD cell harvester (Cambridge Technology, Inc., Watertown, Mass.). The cells were lysed by washing with distilled water and the label bound to the filter was measured by liquid scintillation counting.

As shown in FIGS. 1a–1d, TNF (20 ng/ml) enhanced significantly the $^3$H-thymidine incorporation of B-cell (lane 2) compared to control (lane 1). Addition of monoclonal anti-IL-6 antibodies (1:400), resulted in augmentation of the growth stimulation by TNF (lane 3). Addition of IL-6 (12.5 ng/ml) blunted the growth stimulation induced by TNF, by 35–85%. This observation suggests that IL-6 inhibits the TNF stimulatory effect on B-CLL cells. This effect was seen in additional 5 consecutive patients examined. IL-6 alone, without exogenous addition of TNF, would reduce the $^3$H-thymidine incorporation into B-CLL cells by 12–65%, only in those patients whose leukemic lymphocytes were TNF responsive (FIG. 2).

These results imply that the effects of IL-6 on leukemic B-CLL cells are TNF linked.

The above data are the first to demonstrate direct antagonism of IL-6 to a TNF function; antagonism of IL-6 to TNF production was previously demonstrated by us ([21]) and others ([22]).

EXAMPLE 2

The IL-6 Inhibitory Effect is not Linked to a Specific IL-6 Batch

Figure 3A:
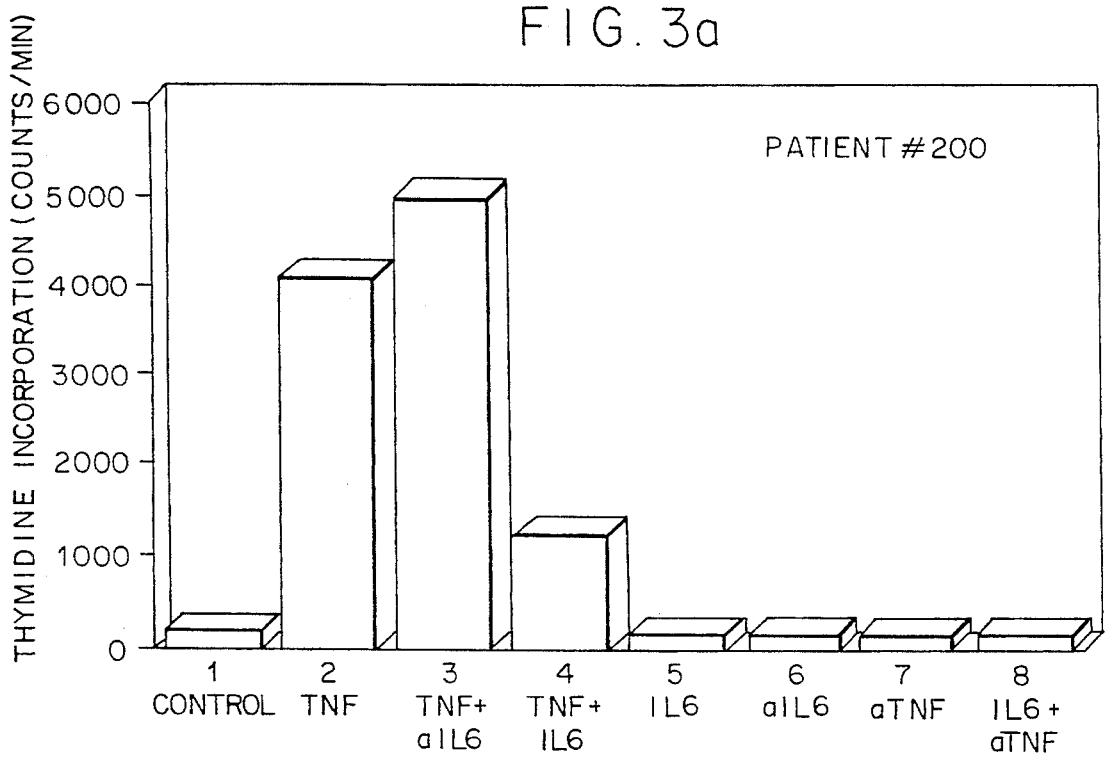
Figure 3B:
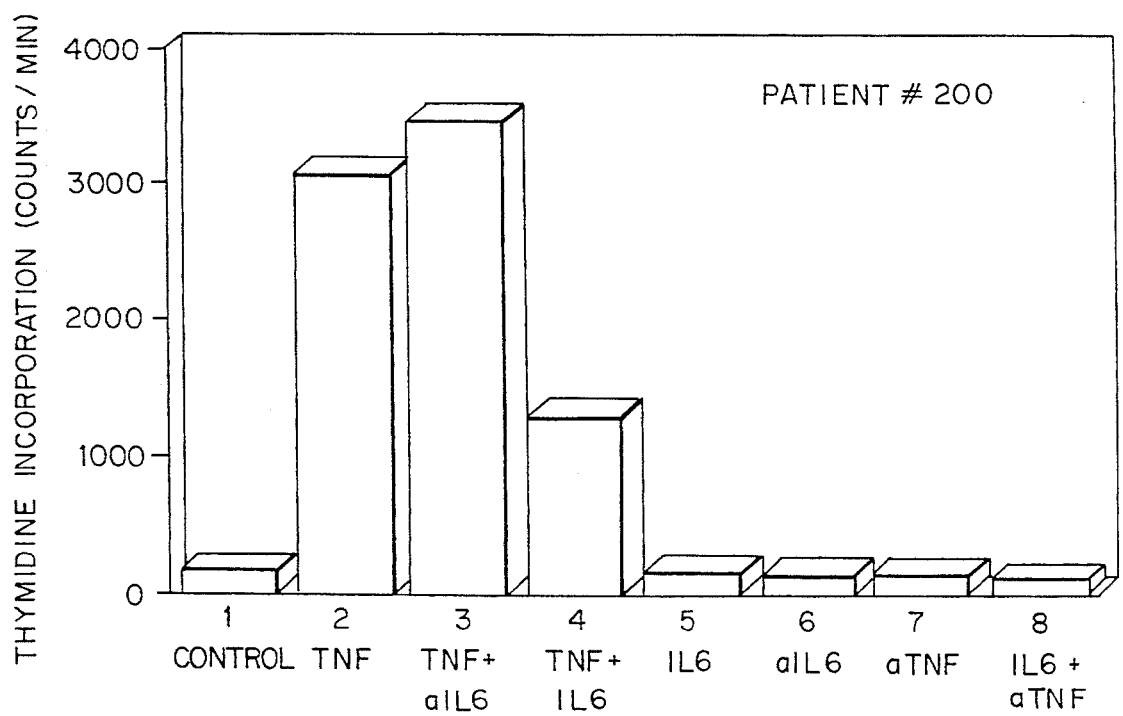

B-CLL leukemic lymphocytes were separated from one donor (# 200), as described in example 1. The cells were incubated in the presence of different recombinant IL-6 batches.

a. A recombinant CHO IL-6 batch, designated batch 1/4 (FIG. 3a).

b. A recombinant CHO IL-6 batch, designated batch 1/17 (FIG. 3b).

c. A recombinant E. coli IL-6 batch (FIG. 3c).

Using identical concentrations of each IL-6 preparation (about 60 u/ml), significant antagonism to the growth stimulatory effector of TNF was obtained with each preparation (FIGS. 3a–c): 70% with the recombinant E. coli batch. This suggested that the inhibitory capacity was not restricted to a specific IL-6 batch or related to a non-specific toxic effect related to some contaminant impurities.

EXAMPLE 3

IL-6 Inhibits the Growth Stimulatory Effects of Lymphotoxin

Figure 4A:
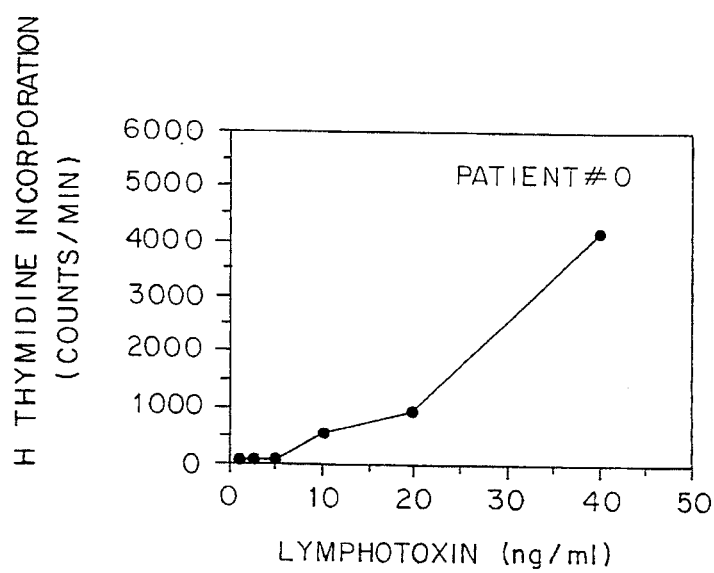
FIGS. 4a–c show the $^3$H-thymidine incorporation into B-CLL lymphocytes of 3 different patients as a function of lymphotoxin (TNF-$\beta$) concentration.
Figure 4B:
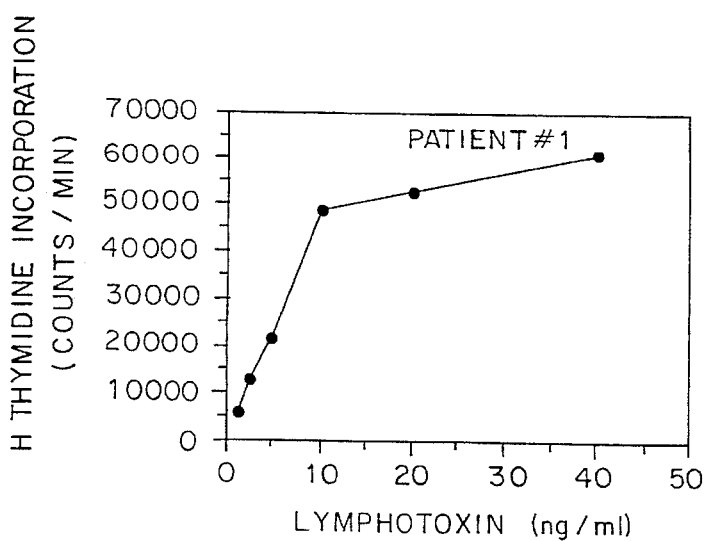
Figure 4C:
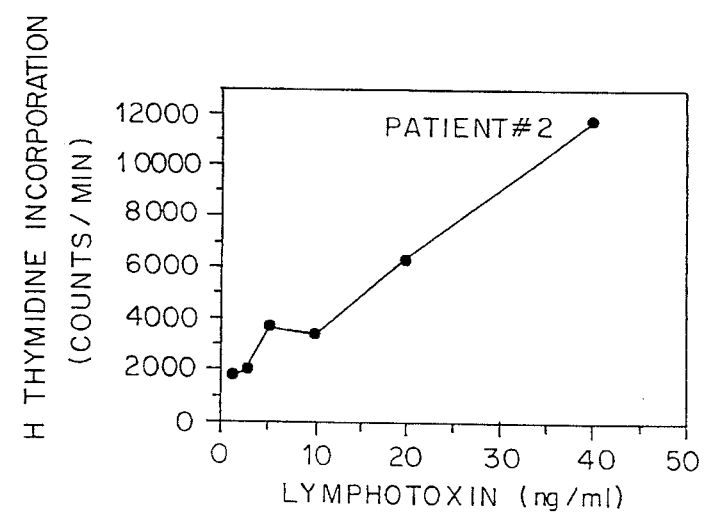

B-CLL cells were separated as described in example 1, and then grown in 96-well plates for 7 days in the presence of lymphotoxin (TNF-β) in increasing concentrations (FIGS. 4a–4c). The $^3$H-thymidine incorporation increased dramatically as a function of the lymphotoxin concentration.

Figure 5:
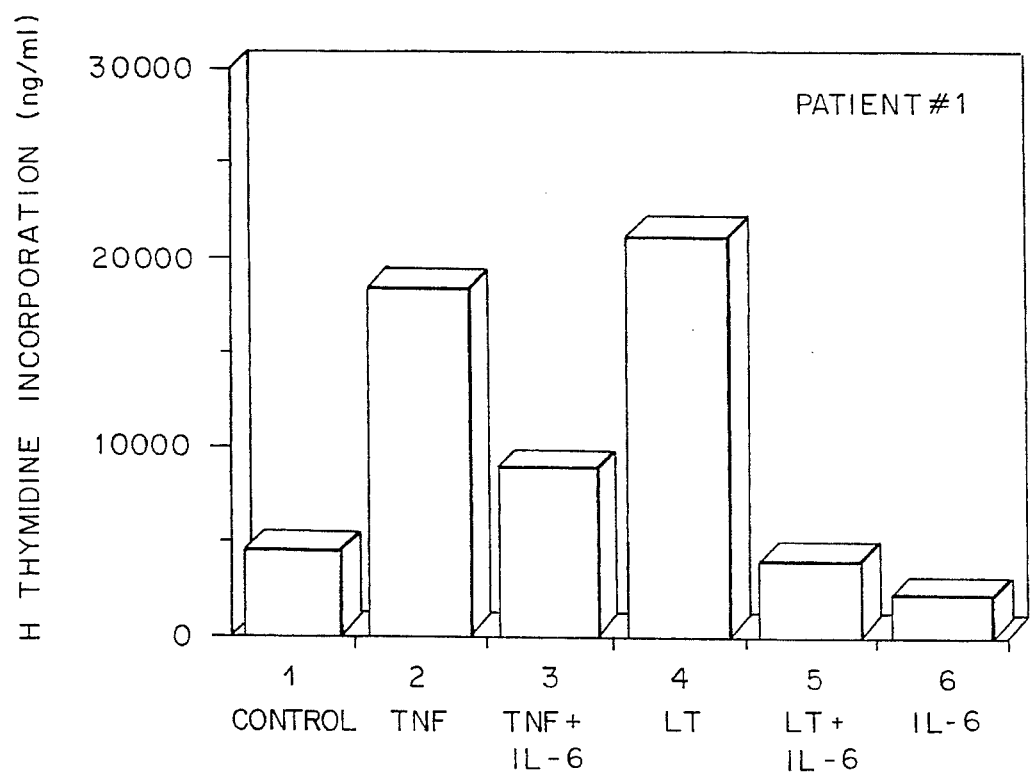
FIG. 5 shows the inhibitory effect of IL-6 on both TNF and lymphotoxin-induced growth of the leukemic B-cells.

When the leukemic cells were grown in the presence in lymphotoxin and IL-6 (about 50 u/ml), the $^3$H-thymidine incorporation was significantly reduced as shown in FIG. 5. This demonstrates the ability of IL-6 to antagonize both TNF-α and TNF-β growth stimulatory effects on B-CLL cells.

EXAMPLE 4

Soluble IL-6 Receptor Supports the IL-6 Inhibition of TNF Effects in B-CLL Cells Additional support to the inhibitory effect of IL-6 on the growth stimulatory effects of TNF on B-CLL leukemic cells was obtained from the incubation of the cells with IL-6 and its soluble receptor (sIL-6 R) (FIGS. 6a–6d).

As previously reported, IL-6 combines with its soluble receptor and the complex binds to an additional cell surface receptor designated gp 130 ($^{18}$). This results in transduction of the IL-6 signal into the cell, with augmentation of its effect.

Figure 6A:
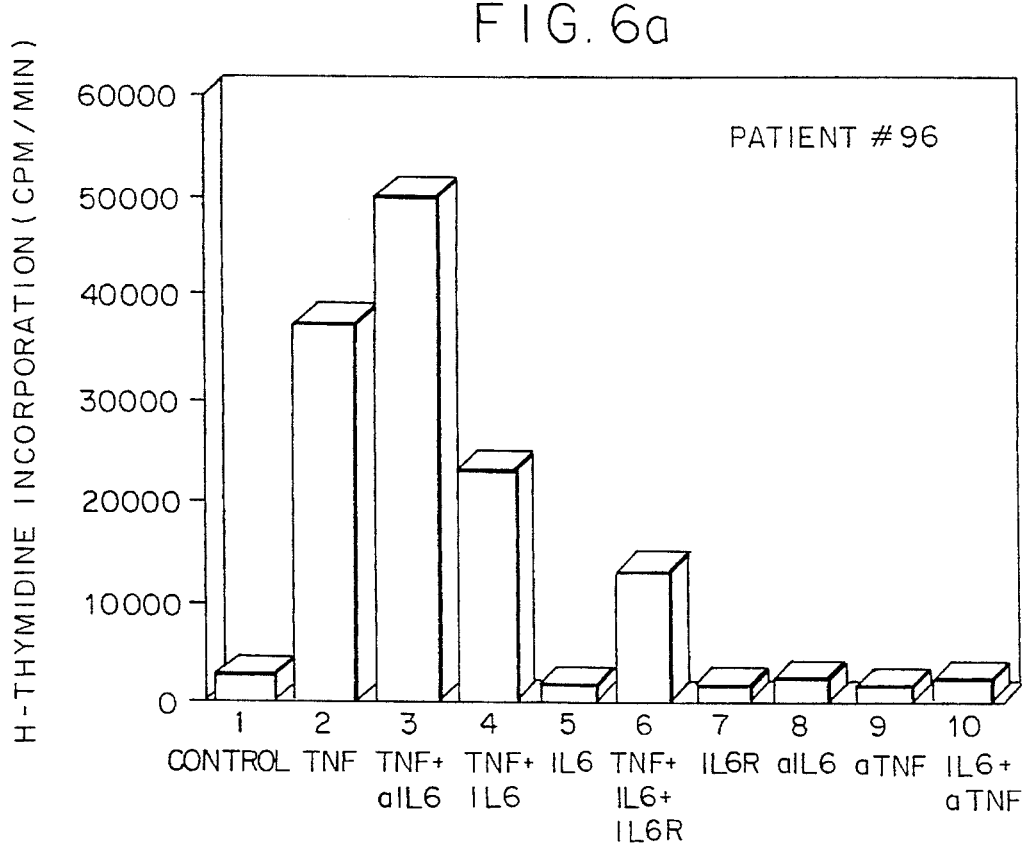
FIGS. 6a–d show the $^3$H-thymidine incorporation by CLL lymphocytes of two different patients (FIGS. 6a and 6b) and the influence of the sIL-6 R on the IL-6 R induced inhibition of the proliferation of the leukemic cells in response to TNF. These responses are compared to those of healthy controls (FIGS. 6c and 6d).
Figure 6B:
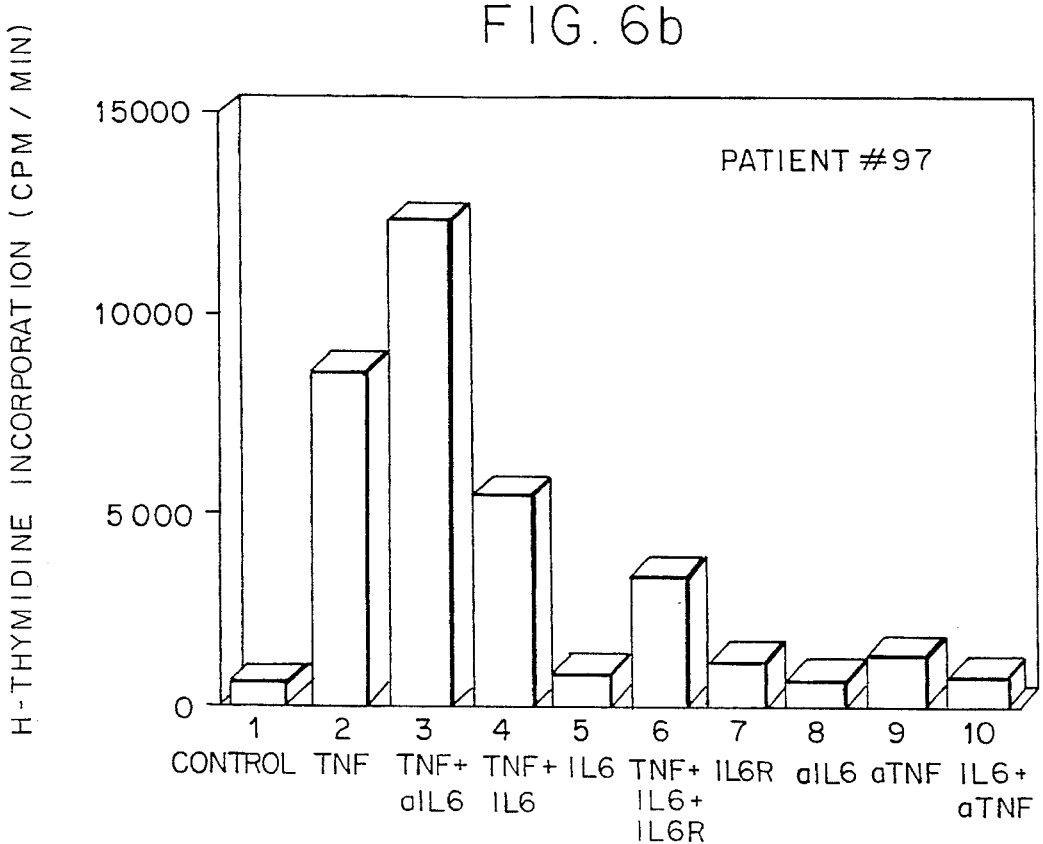
Figure 6C:
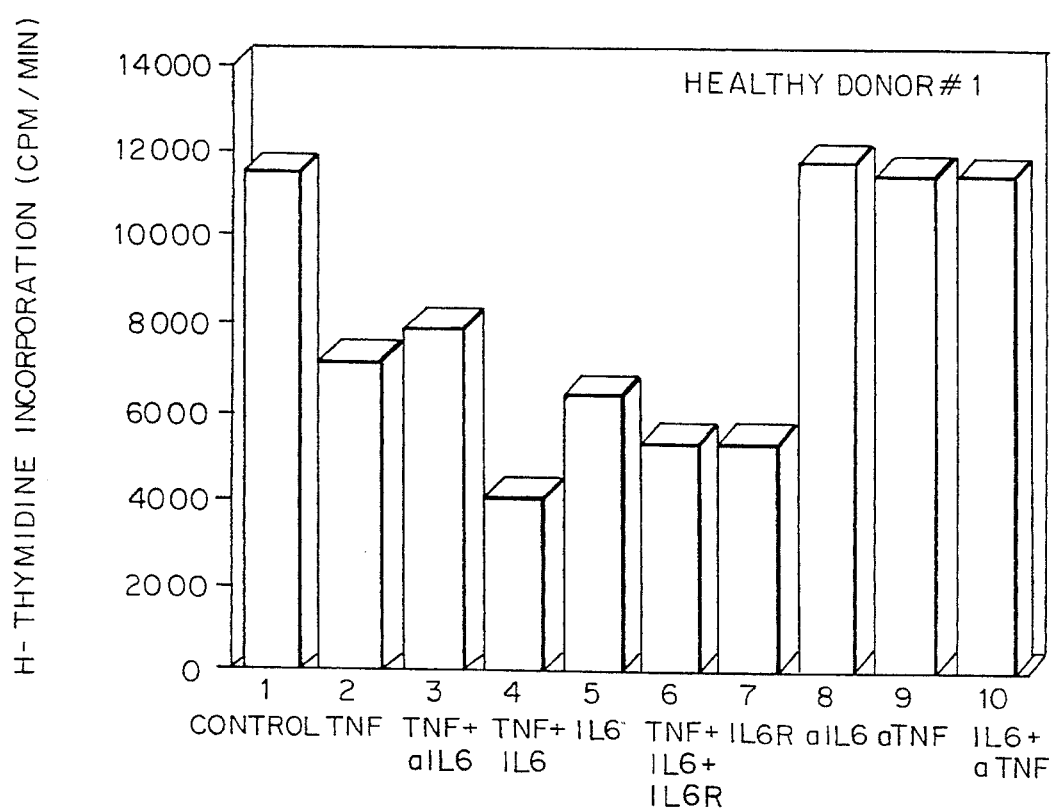
Figure 6D:
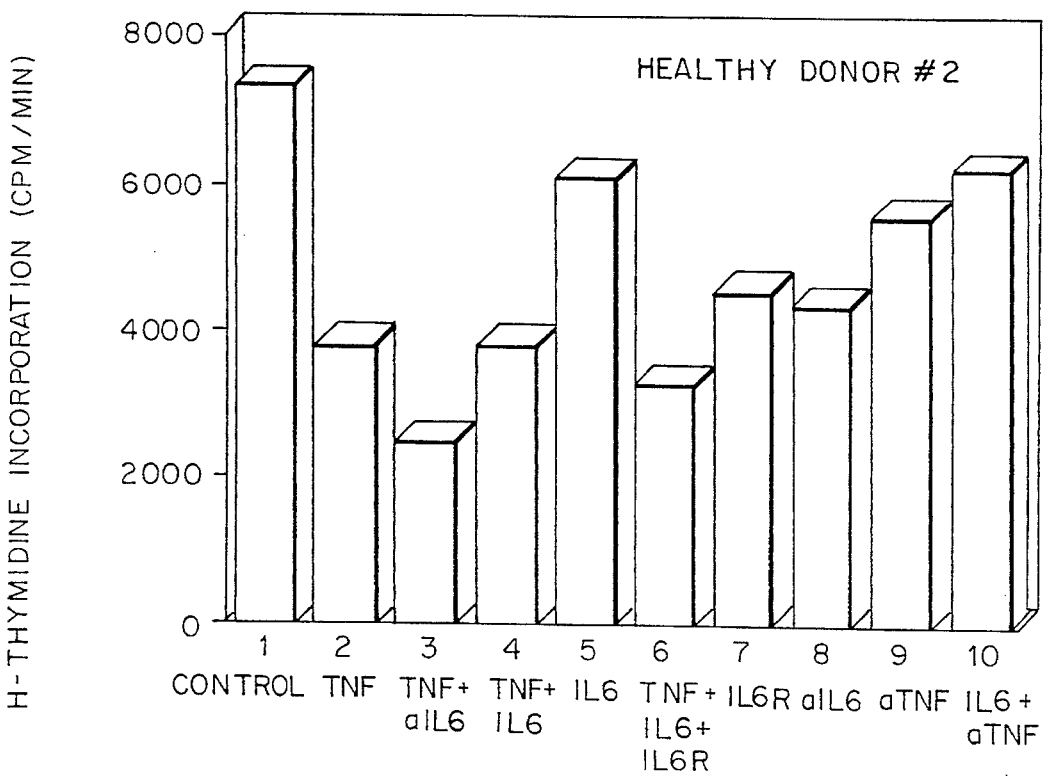
Figure 7A:
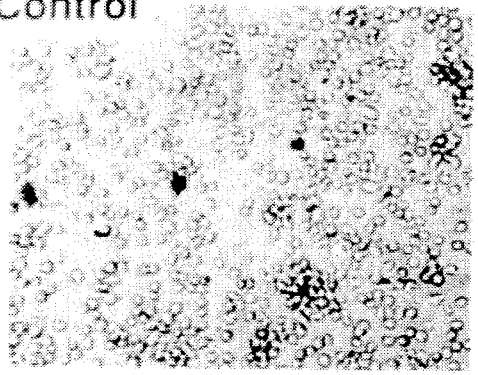
FIGS. 7a–h show photographs of the leukemic cells grown in the presence of IL-6, TNF, IL-6 R, anti IL-6 antibodies, and their different combinations.
Figure 7B:
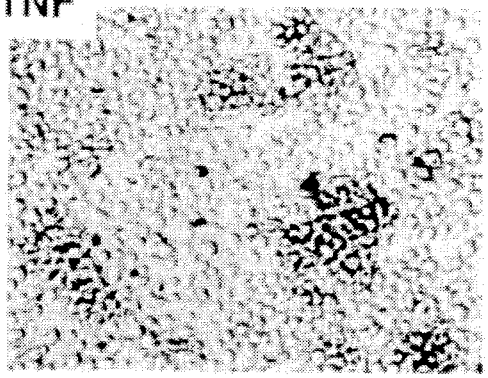
Figure 7C:
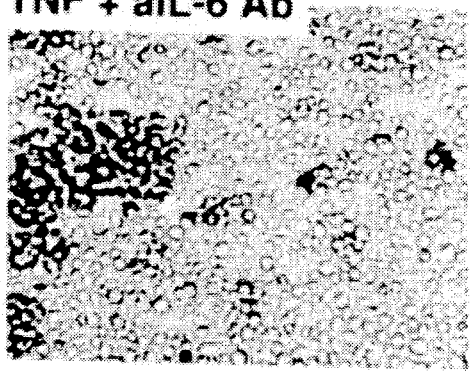
Figure 7D:
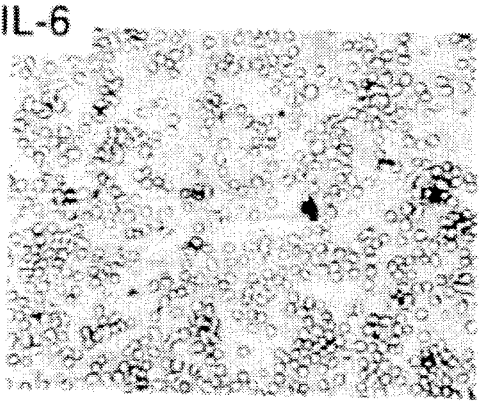
Figure 7E:
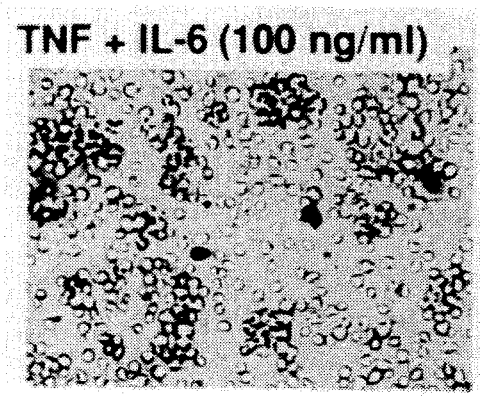
Figure 7F:
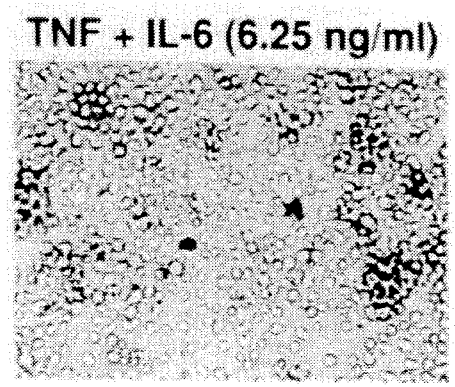
Figure 7G:
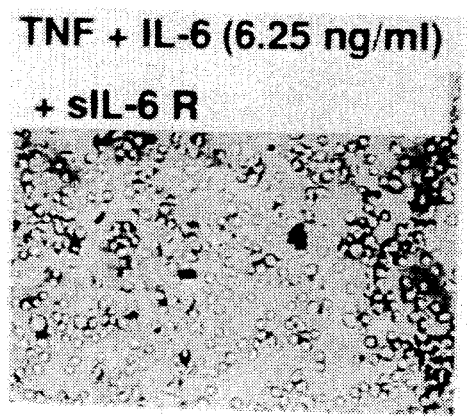
Figure 7H:
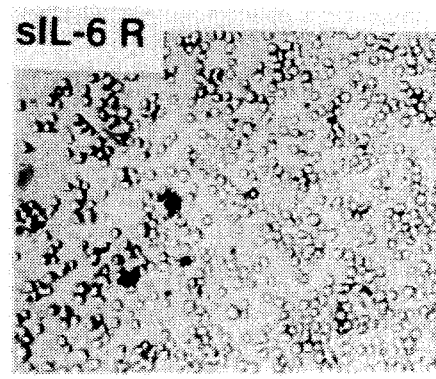
Figure 8A:
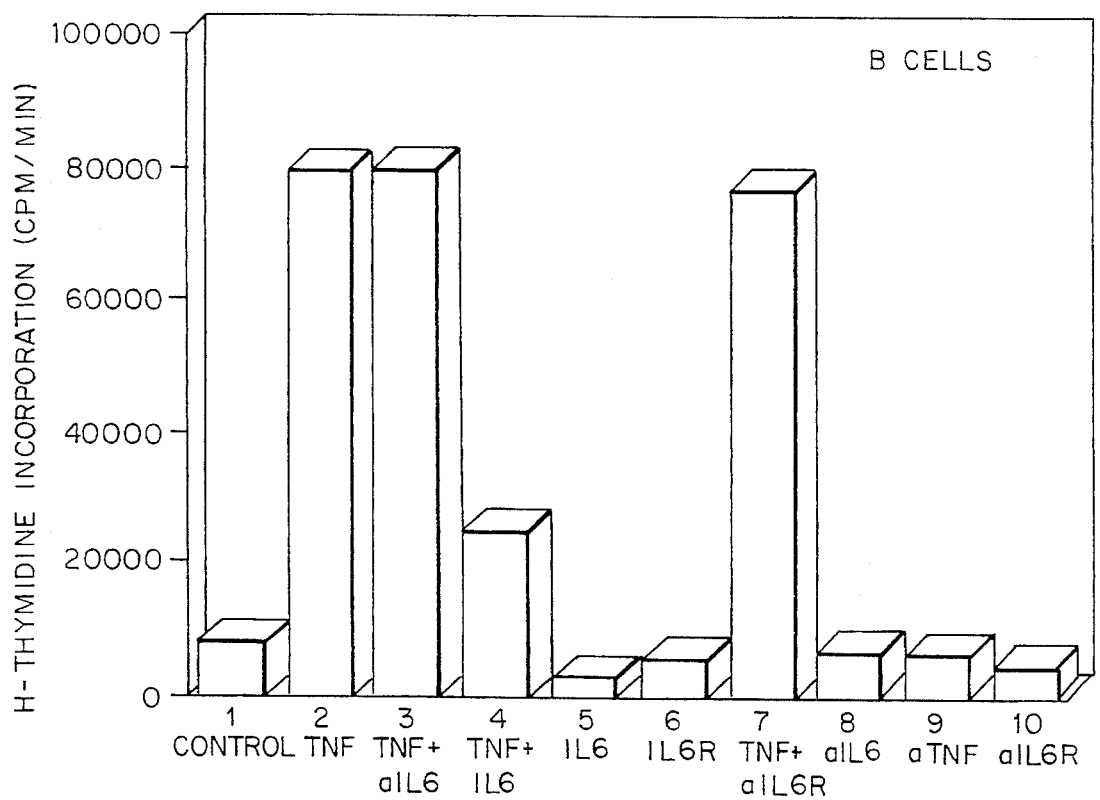
Figure 8C:
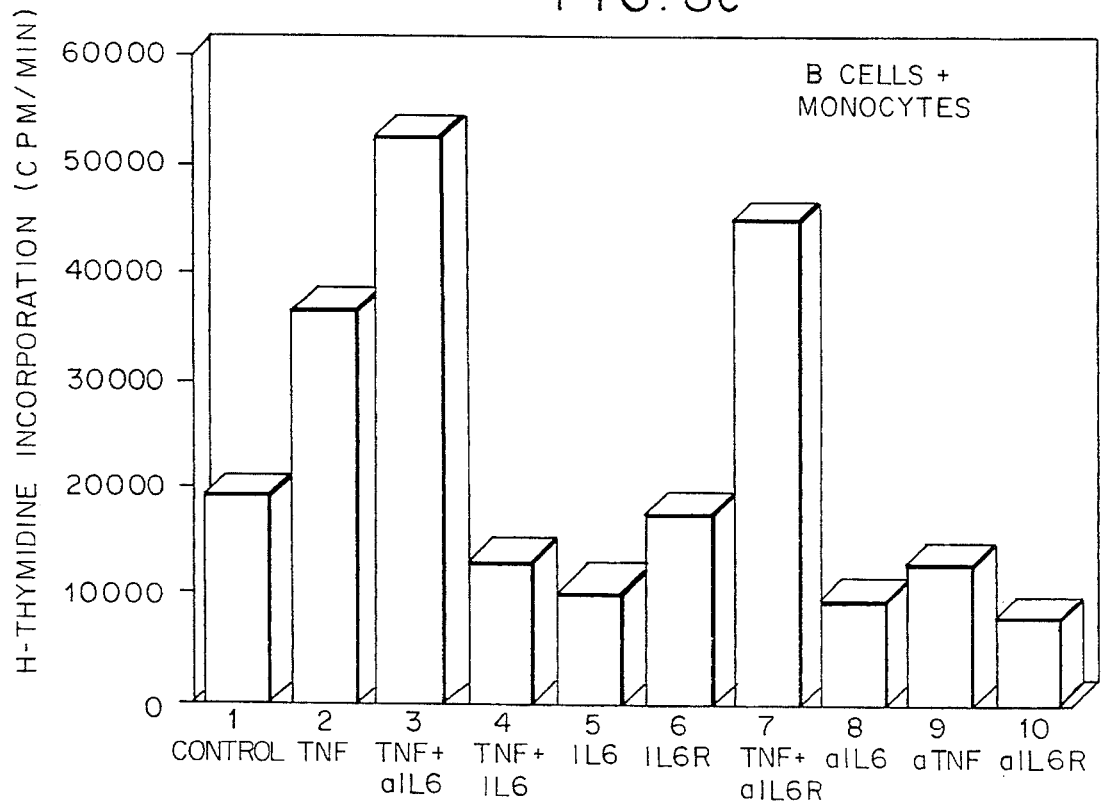

As shown in FIGS. 6a and 6b, IL-6 alone (12.5 ng/ml) reduced the TNF growth stimulatory effects (lane 4) by 34% (donor #96) and 37% (donor #97). The addition of the soluble IL-6 receptor (80 ng/ml) to IL-6 (lane 6) further reduced TNF effects by 65% and 61% respectively.

This observation is an additional support to the antagonism of IL-6 to the growth stimulatory effects of TNF on B-CLL cells.

EXAMPLE 5

IL-6 Inhibits the Multiplication of B-CLL Cells in Response to TNF

B-CLL cells are separated as described in example 1 and grown in the presence of TNF, IL-6, soluble IL-6 receptor and their different combinations (FIGS. 7a–h). IL-6 inhibited significantly the number of cells grown in the presence of TNF. sIL-6 R aided IL-6 to further antagonize the TNF growth stimulatory effects.

EXAMPLE 6

The Antagonism of IL-6 to TNF Effects Persist if B-CLL Cells are Combined with Normal White Blood Cell Elements Further support to the antagonism of IL-6 to the stimulation of TNF to leukemic B-CLL cells is presented in FIGS. 8a–8d.

Mononuclears were separated by Ficoll-Hypaque as described in example 1. Those mononuclears contained B-cells (leukemic), T-cells and monocytes. Part of this cell mixture was subjected to plastic adherence to eliminate monocytes and obtain a mixture of B- and T-cells, and part was incubated with sheep RBC to eliminate T-cells and thus to obtain a mixture of B-cells and monocytes. A part of this mixture was further subjected to plastic adherence in order to eliminate monocytes and obtain pure B-cells (see scheme).

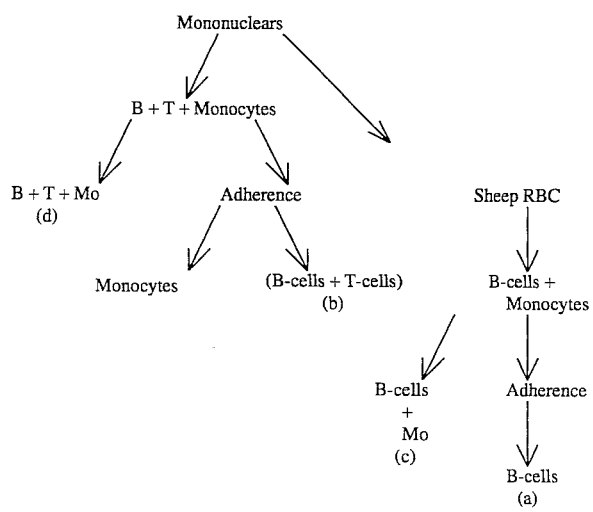

The 4 different populations obtained (a–d in above scheme) were further incubated in 96-well plates at a cell concentration of 300,000 cells/well, and the respective combinations of cytokines, soluble receptors or antibodies were added (see FIGS. 8a–8d).

In mixed cultures of B-cells+Mo or B-cells, T-cells, and monocytes, addition of IL-6 antibodies (polyclonal) to TNF (lane 3) significantly augmented incorporation compared to TNF alone. This suggests autologous IL-6 production by the cells. Addition of polyclonal anti-IL-6-R antibodies (lane 7) augmented TNF's growth stimulatory effects preventing the inhibitionary effects of autologous IL-6 production.

In mixed cultures of B-cells, T-cells and monocytes or B-cells+T-cells, anti-IL-6 antibodies (lane 8) or anti-IL-6 receptor antibodies (lane 10), significantly augmented the $^3$H-thymidine incorporation compared to control cells. Since the antagonism of autologous IL-6 (Table IV) was prevented by antibodies to the cytokine or its receptor, the cells proliferated in response to TNF produced spontaneously by these cultures (Table V). This was determined by a cytotoxic assay as previously reported ($^{23}$).

TABLE IV

| Cell Combinations | Spontaneous IL-6 release by mononuclears (ng/ml) at 48°h | | | | |
|---|---|---|---|---|---|
| | BTM | BT | BM | B | M |
| Healthy donor 1 | 15.1 | 4.32 | — | 3.75 | 15.5 |
| Healthy donor 2 | 11.1 | 3.14 | 26.1 | 3.19 | 12.3 |
| Patient 202 (CLL) | 3.12 | 0 | 3.4 | 0 | 3.81 |
| Patient 203 (CLL) | 1.0 | 0 | 0 | 0 | 2.8 |
| Patient 204 (CLL) | 2.95 | 0.54 | 4.2 | 0 | 3.33 |

TABLE V

| Cell Combinations | Spontaneous TNF release by mononuclears (pcg/ml) at 48°h | | | | |
|---|---|---|---|---|---|
| | BTM | BT | BM | B | M |
| Healthy donor 1 | 70 | 195 | 402 | 116 | 100 |
| Healthy donor 2 | 80 | 45 | 230 | 70 | 28 |
| Patient 202 (CLL) | 25 | 20 | 35 | 15 | 35 |
| Patient 203 (CLL) | 0 | 10 | 28 | 4 | 45 |
| Patient 204 (CLL) | 35 | 46 | 65 | 0 | 132 |

B = B-cells; T = T-cells; M = Monocytes

Having now fully described this invention, it will be appreciated by those skilled in the art that the same can be performed within a wide range of equivalent parameters, concentrations, and conditions without departing from the spirit and scope of the invention, and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Foon, K. A. et al. *Ann. Int. Med.* 113: 525–539 (1990).
2. Kay, N. E. *Br. J. Haematol.* 57: 105–11 (1984).
3. Kay, N. E. *Blood* 57: 418–20 (1981).
4. Platsouces, C. D. et al. *J. Immunol.* 129: 2305–12 (1982).
5. Kay et al. *Blood* 54: 540–4 (1979).
6. Burton, J. D. et al. *Am. J. Hematol.* 30: 61–7 (1989).
7. Juliusson, G. et al. *N.E.J.M.* 323: 720–4 (1990).
8. Falkoff, R. J. M. et al. *J. Immunol.* 131 :801- (1983).
9. Van Damme, J. et al. *J. Exp. Med.* 165: 914–19 (1987).
10. Muraguchi, A. et al. *J. Exp. Med.* 167: 332–44 (1988).
11. Kawano, M. et al. *Nature* 322: 83–4 (1988).
12. Cordingley, F. T. et al. *Lancet* I: 969–71 (1988).
13. Digel, W. et al. *Blood* 73: 1242–46 (1989).
14. Biondi, A. et al. *Blood* 73: 1279–84 (1989).
15. Bianchi, A. C. M. et al. *Nouv. Rev. Fr. Hematol.* 30: 317–19 (1988).
16. Heslop, H. E. et al. *J. Exp. Med.* 172: 1729–34 (1990).
17. Tosato, G. et al. *J. Immunol.* 140: 4329–36 (1988).
18. Taga, T. et al. *Cell* 58: 573–581 (1989).
19. Madsen, M. et al. *J. Immunol. Methods* 33: 323 (1980).
20. Fischer, D. G. et al. *Cell Immunol.* 33: 323 (1980).
21. Aderka, D. et al. *J. Immunol.* 143: 3517–3523 (1989).
22. Schindler, R. et al. *Blood* 75: 40–47 (1990).
23. Aderka, D. et al. *Cancer Res.* Oct. 5, 1991 (In press).

We claim:

1. A method for the treatment of chronic lymphocytic leukemia (CLL) in a patient, comprising administering to said patient a therapeutically effective amount of interleukin-6 (IL-6), a salt, a functional derivative, a mutein, an active fraction, or any combination thereof.

2. A method according to claim 1, further comprising administering a soluble IL-6 receptor in addition to IL-6.

3. A method according to claim 2, wherein said soluble IL-6 receptor is a protein substantially corresponding to recombinant soluble IL-6 receptor.

4. A method according to claim 1, wherein said IL-6 is a protein substantially corresponding to recombinant IL-6.

5. A method according to claim 1, wherein said therapeutically effective amount of IL-6 is sufficient to inhibit the tumor necrosis factor (TNF) proliferation of leukemic lymphocytes in said patient.

6. A method according to claim 1, wherein said IL-6 is administered in the form of a pharmaceutical composition.

7. A method according to claim 6, wherein said pharmaceutical composition further comprises a pharmaceutically acceptable carrier or diluent.

* * * * *